United States Patent [19]
Stanworth et al.

[11] Patent Number: 5,827,668
[45] Date of Patent: Oct. 27, 1998

[54] IMMUNODIAGNOSTIC ASSAY FOR RHEUMATOID ARTHRITIS

[75] Inventors: Dennis Raymond Stanworth, Birmingham; Ian Victor Lewin, Tamworth; Sarita Nayyar, Penn, all of England

[73] Assignee: Peptide Therapeutics Limited, Cambridgeshire, England

[21] Appl. No.: 513,514

[22] Filed: Aug. 10, 1995

Related U.S. Application Data

[63] Continuation of Ser. No. 940,879, filed as PCT/GB91/00821 May 24, 1991, published as WO91/19001 Dec. 12, 1991, abandoned.

[30] Foreign Application Priority Data

May 25, 1990 [GB] United Kingdom ............ 9011702
Jun. 26, 1990 [GB] United Kingdom ............ 9014227

[51] Int. Cl.$^6$ .................... G01N 33/53; G01N 33/48; C07K 16/00; C12P 21/08
[52] U.S. Cl. .................... 435/7.1; 435/810; 435/975; 435/7.92; 436/63; 530/387.1; 530/387.9; 530/388.1
[58] Field of Search .................... 424/185.1; 435/7.1, 435/7.2, 810, 975, 7.92; 436/63; 530/387.1, 387.9, 388.1, 389.1

[56] References Cited

U.S. PATENT DOCUMENTS

| | | |
|---|---|---|
| 3,658,982 | 4/1972 | Reiss et al. . |
| 4,239,743 | 12/1980 | Sedlacek et al. . |
| 4,499,186 | 2/1985 | Teodorescu et al. . |
| 4,544,640 | 10/1985 | Soma et al. . |
| 4,645,748 | 2/1987 | Hurwitz et al. . |

FOREIGN PATENT DOCUMENTS

| | | |
|---|---|---|
| 0 264 219 | 4/1988 | European Pat. Off. . |
| 2 171 999 | 9/1986 | United Kingdom . |
| 85/04422 | 10/1985 | WIPO . |
| WO 88/00240 | 1/1988 | WIPO . |

OTHER PUBLICATIONS

Asakura et al, "Preparation and characterization of monoclonal antibodies against the human thrombin–antithromin III complex" Biochimia et Biophysica Acta, vol. 952, pp. 37–47, 1988.

Vaerman et al, "Complexes of albumin and alpha–antitrypsin with Fc–fragment of IgA monomer are disulfide–bound to penultimate C–terminal cysteine in the Calpha3–domain", Immunology Letters, vol. 15, pp. 67–72, 1987.

Stanworth, "IgA dysfunction in rheumatoid arthritis" Immunology Today, vol. 6, No. 2, 1985.

Waldmann, Science. vol. 252/657, 1991.

Dawes, P.T. et al. British Journal of Rheumat. 1987, 26:351–353.

Nemazee, D.A. et al. "Enhancing antibody: . . . " PNAS, 79:3828–3832 (1982).

Standworth, D.R. et al. "Measurement of IgA" Immunology Letters 11, (1985), pp. 277–280.

Wollheim, F.A. et al. "Plasma alpha 1–anti–trypsin . . . " Penicillamine Res. in Rheumatoid–Disease, Proc. Symp. at Spatlind, Norway, Ed. E. Munthe, Fabritus & Sonner, pp. 152–160 (1976).

Stanwaroth. "The role of IgA in the immunopathogenesis of rheumatoid arthritis" Chap. 7 in Immunogenic Mechanisms of Arthritis, Eds. J. Goodacre & D.W. Carson, pp. 122–142, MTP Press (1987).

Stanworth in "Modulation of autoimmunity & disease" eds. Maini and Berry, Praeger, pp. 31–35 (1981).

Stanworth, D.R. "IgA dysfunction in rheumatoid arthritis" Immunology Today, 6 43–45 (1985).

Stanworth, D.R. "The role of IgE and IgA in rheumatoid arithritis", Hungarian Rheumatol/Suppl (Proc. Eular. Symp. Budapest, 1984 on Current Immunological Concepts in Rheumatology), 9–16 (1985).

Long et al. Chemical Abstracts 101, #145029e, (1984).

*Primary Examiner*—Sheela Huff
*Assistant Examiner*—Yvonne Eyler
*Attorney, Agent, or Firm*—Nixon & Vanderhye P.C.

[57] ABSTRACT

The assay of rheumatoid arthritis by reference to IgA-$\alpha_1$ antitrypsin complex present in analytes is facilitated by certain novel antibody reagents. These are ligands comprising an antibody domain specific for an antigenic determinant of a complex of human IgA and $\alpha_1$-antitrypsin, this antibody domain being substantially non reactive with free human IgA and free human $\alpha_1$-antitrypsin. Monoclonal antibodies to the naturally occurring IgA-$\alpha_1$AT complex and monoclonal or polyclonal antibodies to a synthetic peptide are preferred. The synthetic peptide in itself part of the invention and preferably has an amino acid sequence: Val-Ser-Val-Val-Met-Ala-Glu-Val-Asp-Gly-Thr-Cys-Tyr (SEQ ID NO:2)

15 Claims, No Drawings

IMMUNODIAGNOSTIC ASSAY FOR RHEUMATOID ARTHRITIS

This is a Rule 60 continuation of application Ser. No. 07/940,879, filed as PCT/GB91/00821 May 24, 1991, published as WO91/19001 Dec. 12, 1991, now abandoned.

BACKGROUND OF THE INVENTION

1. Field of the Invention

The present invention is directed to a method of assay of rheumatoid arthritis (RA). More particularly, the present invention is directed to the assay of human immunoglobulin A-$\alpha_1$-antitrypsin complex (IgA-$\alpha_1$AT) in patients who are suspected of having or are being treated for RA.

2. Description of the Prior Art

Rheumatoid arthritis has been described as an unresolved systemic inflammation in which immune dysfunction and genetic susceptibility play roles. In earlier stages, it is often characterised by fluctuating remissions and exacerbations, and in later stages by a chronic granulatamous response (pannus formation) leading to tissue destruction notably of bone and cartilage. The synovial membrane in RA has many of the characteristics of a hyperactive immunologically stimulated lymphoid organ and the ratio of T suppressor to T helper lymphocytes has been shown to be significantly reduced.

Since there is no unambiguous test distinguishing RA from other acute or chronic inflammatory diseases, differentiating RA from other arthritides, such as systemic lupus erythematosus (SLE), ankylosing spondylitis (AS), polyarticular gout (PAG), or psoriatic arthritis (PsA) is often difficult. Diagnosis of RA is usually made according to American Rheumatism Association (ARA) criteria, i.e.:

(1) morning stiffness;
(2) joint tenderness or pain on motion;
(3) soft-tissue swelling of the joint;
(4) soft-tissue swelling of a second joint (within three months);
(5) soft-tissue swelling of symmetrical joints (excludes distal interphalangeal joint);
(6) Subcutaneous nodules;
(7) X-ray changes;
(8) Serum positive for rheumatoid factors;

wherein diagnosis of 3 or 4 of these factors is considered representative of probable RA and diagnosis of 5 or more of the factors is considered representative of definite RA.

The most widely used immunodiagnostic assay of RA, the so-called Waaler-Rose assay, is based upon an antibody (rheumatoid factor) to the Fc region of IgG. Rheumatoid factor (RF) is present in about 60% to 70% of those individuals afflicted with RA. The test is not satisfactory because it has been found to give unacceptably large numbers of false positives or negatives, and it does not assess the response to therapy or predict activation or reactivation of the disease process. Moreover, based as it is on a haemagglutination or latex agglutination end point, it is difficult to standardize from one clinical laboratory to another. More seriously, it can provide a positive result on only about 70%. of chronic sufferers from this disease and, in any case, the immunopathogenic role of RF has never been established.

Recently, evidence has begun to point to the covalently linked (S—S) complex between IgA and $\alpha_1$-antitrypsin ($\alpha_1$AT) as a major immunopathological factor in RA. This complex is found at grossly elevated levels in the sera of patients with IgA myelomatosis but has also been detected in abnormally high amounts in the circulation of RA patients. The following evidence suggests that the measurement of circulating levels of IgA-$\alpha_1$AT complex would provide a more relevant immunodiagnostic indicator of-rheumatoid arthritis than those currently used:

(1) It is present in abnormally high levels in the circulation and joint fluids of virtually all patients with untreated chronic rheumatoid arthritis. (The currently utilized rheumatoid factor is detectable in the sera of only about 70% of such patients).

(2) The serum level of IgA-$\alpha_1$AT complex appears to fall in those patients who show a beneficial clinical response to treatment with second line anti-rheumatic drugs.

(3) It is also detectable at abnormally high levels in those AS patients who show erosive joint changes.

(4) Unlike other so-called disease markers which are measured in RA, such as rheumatoid factor and acute phase proteins (e.g., haptoglobin and C-reactive protein), both in vitro and in vivo studies have provided a plausible explanation of the immunopathogenicity of the IgA-$\alpha_1$AT complex. Thus, not only can the formation of the IgA-$\alpha_1$AT complex lead to the consumption of as much as one-third of the total available $\alpha_1$AT (one of the major anti-proteases) in rheumatoid patients' serum or joint fluids, but the IgA-$\alpha_1$AT complex itself is capable of eliciting release of degradative proteolytic enzymes from isolated macrophages (by a cytolytic process dependent on the activation of the alternative complement pathway). Furthermore, injection of the isolated complex into normal rabbits' knee joints results in the rapid development of an acute arthritis, which shows the gross anatomical and histopathological features of the clinical condition. (See, Stanworth, D. R., "IgA dysfunction in rheumatoid arthritis", Immunology Today, New Directions in Research, 6. pp. 43–45 (1985); Stanworth D. R. "The role of IgA in the immunopathogenesis of rheumatoid arthritis" Chapter 7 in "Immunogenic Mechanisms of Arthritis" Eds. J. Goodacre and D. W. Carson, pp 122–142 (1987) and Dawes, P. T., Jackson R., Shadforth, M. F., Lewin, I. V., and Stanworth, D. R., "The relationship between the complex of immunoglobulin A and $\alpha_1$-antitrypsin, its constituent components and the acute phase response, as. measured by C-reactive protein in rheumatoid arthritis treated with gold or D-penicillamine", British Journal of Rheumatology, 26. pp. 351–353 (1987)).

The current method of measuring IgA-$\alpha_1$AT complex relies on a two-dimensional immunoelectrophoresis comprising a first dimensional electrophoretic separation of complex from free $\alpha_1$AT in agarose, and its identification by second dimensional electrophoresis into agarose-containing antiserum directed specifically against $\alpha_1$AT. The amount of complex is then quantitated (in arbitrary units) by determining the area under its precipitation peak (on the subsequently dried and stained plate) by planimetry. However, this is a laborious and time-consuming procedure.

Accordingly, it would be desirable to provide an easily performed assay for the IgA-$\alpha_1$AT complex. Initial attempts were made to use an ELISA in which either anti-IgA or anti-$\alpha_1$AT antibody was first coated onto the wells of micro-titration plates followed by incubation with an IgA-$\alpha_1$AT complex-containing test specimen, reaction with either anti-$\alpha_1$AT IgG or anti-IgA IgG antibody, respectively and final development with an enzyme labelled anti-IgG antibody. However, it is a problem that such a complex cannot be detected reliably by an assay which depends on the binding of the IgA-$\alpha_1$AT complex to an antibody to IgA or $\alpha_1$AT, since this approach would result in the binding of uncomplexed IgA or $\alpha_1$AT which are also present in unquantified amounts in the sample from the patient, thus interfering with the quantitative measurement of the IgA-$\alpha_1$AT complex.

It has been necessary, therefore, to produce an antibody directed specifically against human IgA-$\alpha_1$AT complex. An initial attempt to accomplish this by immunising rabbits with purified IgA-$\alpha_1$AT complex failed, as the resultant antisera reacted also with uncomplexed IgA and $\alpha_1$AT.

SUMMARY OF THE INVENTION

It has surprisingly been found that a monoclonal antibody can be produced which is virtually unreactive with free IgA and $\alpha_1$AT, but is specific to the naturally occurring IgA-$\alpha_1$AT complex. Moreover, when attempting to prepare such antibodies from the fusion of mouse spleen cells with myeloma cells, it was found that yields of fused spleen cells were very low, making the production of the hybridomas impossible. It was necessary to find a solution to this problem, which, as it transpired, was caused by toxicity of the human IgA-$\alpha_1$AT complex to the mouse macrophages. It was demonstrated that incubation of isolated peritoneal mouse macrophages with human IgA-$\alpha_1$AT complex leads to a substantial release of the cytoplasmic enzyme LDH and a subsequent destruction of the macrophages. The problem was eventually overcome as described below.

Furthermore, an immunogenic peptide has been synthesised comprising a first peptide fragment having an amino acid sequence or an analogue thereof found in the Fc region of human IgA and a second peptide fragment having an amino acid sequence or an analogue thereof found in human $\alpha_1$AT, said first and second fragments being covalently bound to one another, wherein an antibody raised against said peptide is substantially non-reactive with free human IgA, is substantially non-reactive with free human $\alpha_1$AT, and binds to the naturally-occurring complex of human IgA and $\alpha_1$AT (IgA-$\alpha_1$AT). Surprisingly. polyclonal antibodies raised against the said peptide were also found to be substantially non-reactive with free IgA and $\alpha_1$AT. Monoclonal antibodies of the same or better specificity will doubtless be raisable against it. Moreover, the recently developed chimeric antibodies (Reichman, L., Clark, M., Waldmann, H. and Winter G., Nature 332, pp 323–327, 1988)), single chain antibodies (PCT Patent Application Publication Number WO 88/01649 Genex Corporation) and single domain antibodies (Ward, E. S., Güssow, D., Griffiths, A. D., Jones, P. T. and Winter, G. Nature 341. pp 544–546, (1989)) having elements anti to the said naturally occurring complex and peptide can be expected to be producible.

Accordingly the invention provides a ligand comprising an antibody domain specific for an antigenic determinant of a complex of human IgA and $\alpha_1$-antitrypsin, said antibody domain being substantially non-reactive with free human IgA and free human $\alpha_1$-antitrypsin.

The invention also provides a method of assay of rheumatoid arthritis (RA) in an analyte suspected to contain a complex of human IgA and $\alpha_1$-antitrypsin (IgA-$\alpha_1$AT) as an indicator of RA, which comprises detecting or measuring immunological binding between the said complex and the above said ligand.

This invention further provides an assay kit for carrying out a method of assay of human RA in an analyte suspected to contain a complex of human IgA and $\alpha_1$-antitrypsin (IgA-$\alpha_1$AT) as an indicator of RA, the kit comprising an IgA-$\alpha_1$AT complex and a ligand whose antibody domain is specific for an antigenic determinant of IgA-$\alpha_1$AT, but substantially non-reactive with free human IgA and free human $\alpha_1$AT.

DESCRIPTION OR THE PREFERRED EMBODIMENTS

The following definitions are used throughout the present specification:

"Assay" means a method of detection or measurement.

"IgA-$\alpha_1$AT complex" means the complex as found in human patients serum, unless otherwise stated or the context otherwise requires.

Fab' fragment represents one "arm" of the two "arms" of the "Y" shaped antibody configuration; the fragment retains antigen-binding ability.

F(ab')2 fragment represents two Fab' "arms" linked by disulphide bonds; the fragment retains antigen-binding ability.

Fc fragment represents the single "tail" or central axis of the "Y" shaped antibody.

The ligands of the invention comprise an antibody domain specific for an antigenic determinant of a complex of human IgA and human $\alpha_1$AT (IgA-$\alpha_1$AT). The said antibody domain is relatively non-reactive with free human IgA and free $\alpha_1$AT. The complex of IgA and $\alpha_1$AT (IgA-$\alpha_1$AT) is the naturally occurring complex found in analytes taken from patients suffering from rheumatoid arthritis. Most preferably, but as exemplified below, not necessarily, the ligand comprises a monoclonal antibody raised against such a complex. The most preferred monoclonal antibodies are obtainable from hybridomas which are the subject of patent deposits described herein below. Polyclonal antibodies raised against the purified, naturally occurring, complex were not found to be specific for the IgA-$\alpha_1$AT complex, the resulting antisera reacting also with uncomplexed IgA and $\alpha_1$AT.

Alternatively the ligand can be an antibody raised against a synthetic peptide of the invention. This synthetic peptide is a covalently linked conjugate of short chain peptides representative of those parts of the IgA heavy chain and $\alpha_1$AT chain sequences which comprise an IgA-$\alpha_1$AT complex-specific immunogenic determinant. In a particular embodiment, the present invention provides and utilizes a first peptide fragment having an amino acid sequence found in the Fc region of human IgA or an analogue of said sequence, and a second peptide fragment having an amino acid sequence found in human $\alpha_1$AT or an analogue of said sequence. which are covalently bound to one another. The preferred form of covalent bonding is an S—S linkage which preserves the immunogenic three dimensional conformation of the linkage of the penultimate cysteine residue, relative to the C-terminal end of human IgA, in the Fc region of human IgA to human $\alpha_1$AT. The structure of the preferred IgA-$\alpha_1$AT complex has not yet been completely elucidated. However, it is likely that the covalent S—S bridging occurs between the only cysteine residue (No. 232) of human $\alpha_1$AT and the cysteine residue (No. 495) occupying the penultimate cysteine position in the $\alpha$-chain of human IgA, to which J-chain is known to conjugate in the formation of polymeric IgA.

The first peptide fragment preferably corresponds to an amino acid sequence of the Fc region of human IgA containing the penultimate cysteine residue, relative to the C-terminal end of human IgA, comprising 5 to 20 amino acid residues, preferably 10 to 15 amino acid residues, or analogues thereof. The first peptide fragment preferably contains at least the amino acid sequence Val-Met-Ala-Glu-Val-Asp-Gly-Thr-Cys-Tyr (SEQ ID NO: 1) which corresponds to residues 487–496 of the human IgA $\alpha$-chain, or an analogue thereof. This is the minimum sequence length which will lead to the formation of a stable conjugate. Most preferably the amino acid sequence comprises Val-Ser-Val-Val-Met-Ala-Glu-Val-Asp-Gly-Thr-Cys-Tyr (SEQ ID NO: 2) which corresponds to residues 484–496 of the human IgA α-chain or an analogue thereof.

The second peptide fragment preferably corresponds to an amino acid sequence of human $\alpha_1$AT, including the cysteine residue which bonds covalently to the IgA α-chain, comprising 5 to 20 amino acid residues, preferably 10 to 15 amino acid residues, or analogues thereof. The second peptide fragment preferably comprises at least the amino acid sequence His-Cys-Lys-Lys (SEQ ID NO: 3)

which corresponds to residues 231–234 of human $\alpha_1$-AT, or an analogue thereof. This is considered to be the minimum sequence length which will lead to the formation of a stable conjugate. Most preferably the amino acid sequence comprises Gly-Met-Phe-Asn-Ile-Gln-His-Cys-Lys-Lys-Leu-Ser-Ser (SEQ ID NO: 4) which corresponds to the residues 225–237 of the human $\alpha_1$-AT or an analogue thereof.

Accordingly, a particularly preferred immunogenic peptide of this invention comprises at least the following amino acid sequence:

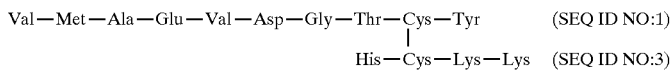

or an analogue thereof.

Most preferably, the immunogenic peptide comprises the peptide conjugate of the following amino acid sequence:

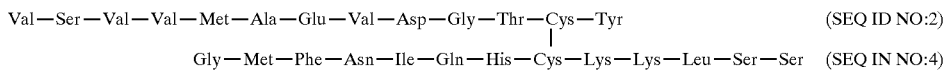

or an analogue thereof (hereinafter designated peptide F017-F018).

Antibodies to the IgA-$\alpha_1$AT complex (whether the natural complex or synthetic peptide) may be readily prepared by techniques well-known in the art. Thus, polyclonal antibodies can be obtained from immunised rabbits by exsanguination. Monoclonal antibodies can be prepared by the Köhler-Milstein method in mice provided that spleen cells are always used in excess in the fusion and that cytolysis of the resultant hybridomas is combatted as necessary by addition of fresh spleen cells. The hybridomas have then to be screened for specificity to the complex. Fab' and F(ab')2 fragments of such monoclonal or polyclonal antibodies may be prepared in well-known ways. Any of these molecules providing antibody domains to the complex can be used.

For diagnostic purposes, the antibody will react with the naturally occurring IgA-$\alpha_1$AT complex from the individual under test to produce a detectable product. An antibody composition used in any test designed to quantitate the presence of IgA-$\alpha_1$AT must contain sufficient antibody to react with all of the naturally occurring IgA-$\alpha_1$AT complex. Such diagnostically effective amounts of antibody will vary appreciably with a number of factors well known to those skilled in the art. These include, for example, the sensitivity and specificity of the test employed, the instrumentation available and the amount of analyte under test. The most preferred analyte is a serum sample since this gives a better indication of RA than joint fluids.

Detection and measurement of levels of the IgA-$\alpha_1$AT complex, preferably in serum or joint fluid, may also be used as a prognostic indicator of RA in order to facilitate the better management of patients with "early" (pre-erosion stage) RA, where diagnosis is normally difficult.

While enzyme-linked immunosorbent assay (ELISA) is preferred in this invention, other assays, e.g. radioimmunoassay, precipitation, agglutination, direct and indirect immunofluorescence and complement fixation can be used. These assays may employ any protocol such as competitive, inhibition or sandwich type.

The assays generally require a detectable label. The anti-IgA-$\alpha_1$AT antibody, an anti-antibody (e.g. goat anti-rabbit serum), an anti-IgA antibody or an anti-$\alpha_1$AT antibody may be labelled. Useful labels include fluorescent labels such as fluorescein, rhodamine or auramine and radioisotopes such as $^{14}$C, $^{131}$I, $^{125}$I and $^{35}$S. The preferred enzyme labels include horseradish peroxidase, β-D-glucosidase, β-D-galactosidase, urease, glucose oxidase plus peroxidase, and acid phosphatase.

Currently available procedures for detecting the aforementioned labels are well-known and include calorimetric, luminometric and fluorometric techniques, as well as various instrumental methods of detecting radio isotopes.

The assays will normally be carried out so that the detectable product becomes bound to a support, so as to ensure ready separation from the unbound serum sample.

Usable supports include glass or plastic surfaces, especially the inner surface of test tubes or a surface of a test plate. Typical examples of flat surfaces useful in the enzyme-linked immunoassay procedure (ELISA) or the radioimmunoassay procedure (RIA) include glass, nitrocellulose paper or plastics such as polystyrene, polycarbonate or various polyvinyls. Particles which can be used for macroscopic procedures wherein the reaction product can be detected visually, e.g. the hempgglutination procedure, include biological particles such as sheep red blood cells or human group O red blood cells, and biologically inert particles such as charcoal, bentonite or latex beads. Such beads can be formed of polystyrene, polyvinylpyrrolidone or various polyvinyls.

Attachment to the support surface may be by direct adsorption, forced adsorption or chemical coupling in accordance with known procedures.

Preferred binding schemes are as follows (*=labelled substance):

Sandwich Assays support/anti-IgA-$\alpha_1$AT/IgA-$\alpha_1$AT analyte/anti-IgA*;

support/anti-IgA-$\alpha_1$AT/IgA-$\alpha_1$AT analyte/anti-$\alpha_1$AT*;

support/anti-IgA-$\alpha_1$AT/IgA-$\alpha_1$AT analyte/anti-IgA-$\alpha_1$AT*

(the 2nd antibody having a different specificity from the first)

Inhibition Assays

Support/IgA-$\alpha_1$AT/anti IgA-$\alpha_1$AT*+analyte (pre-incubated before addition to support/IgA-$\alpha_1$AT)

Competition Assays

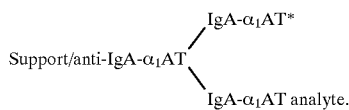

A wide variety of kits are possible for carrying out assays of the present invention. They comprise a ligand of the invention and an IgA-$\alpha_1$AT complex. Preferably the assay kit will provide a means of assaying the complex either by (A) a sandwich assay wherein the kit provides in addition to the above, a second detection ligand which comprises an antibody domain capable of detecting an IgA-$\alpha_1$AT complex when bound to the first ligand, or (B) a competitive or inhibition assay in which the said IgA-$\alpha_1$AT complex component of the assay kit is an immunogenic analogue, and is more preferably an immunogenic synthetic peptide, of the naturally occurring complex. The ligands are preferably polyclonal or monoclonal antibodies as set forth above and Fab' or F(ab')2 fragments thereof or single domain or single chain antibodies as will be apparent to one skilled in the art.

The detection ligand in a sandwich assay need not be an antibody which has specificity to the whole complex. Any such ligand which provides a means of attaching label to the analyte IgA-$\alpha_1$AT (without interfering with the binding of the analyte to the capture antibody) is usable. Thus it could conveniently be an antibody raised against IgA or $\alpha_1$AT.

The detection ligand in the sandwich assay, the antibody which competes with the analyte in a competition assay and the antibody which is pre-reacted with the analyte in an inhibition assay have to be labelled at some stage. While these reagents can be provided as ready labelled conjugates it is normally more convenient merely to label them by providing a further antibody thereto which is labelled as a separate component. Typically the second antibody is an immunoglobulin and the further antibody provides anti-immunoglobulin by being raised in a different host animal.

Normally, all components of the kit will be provided in separate containers.

Appropriate washing, enzyme substrate and buffer solutions would be provided with the assay kit, together with a detailed instruction sheet, including advice on the calculation and interpretation of the results.

Although the synthetic peptide or purified naturally occurring IgA-$\alpha_1$AT complex (being covalently linked) is relatively stable, it could become dissociated if test samples were mishandled (e.g. exposed to reducing conditions).

It is important to keep analytes such as specimens of sera and joint fluids at 4° C. over the short term, awaiting assay. If, however, they cannot be tested within a day or two they should be stored in the frozen state (at or preferably below −20° C.), after having had cellular and non-cellular debris removed from them by gentle centrifugation.

The following Examples illustrate the invention. "Tween" is a Registered Trade Mark.

EXAMPLE 1
Formation of mixed disulphide between peptides F017 and F018

Both peptides F017 and F018 were synthesized using the 9-fluorenylmethoxycarbonyl (Fmoc) solid phase peptide synthesis chemistry in an LKB Biolynx 4170 peptide synthesizer. The cysteine (Cys) residues in both peptides F017 and F018 had side-chain protection of S-triphenylmethyl (TRT).

15 mMol Iodine in acetic acid: water (8:2) was added to a mixture of 5 mMol F018 and 5 mMol F017 in acetic acid-water (8:2). The mixture was gently mixed on addition and then left at 4° C. for 16 hours.

Peptides F017-F018 were also treated in a similar way separately to act as controls. Each peptide preparation was then run on a Nucleocil 5 C18 reverse-phase HPLC column with a methanol gradient (A=5% methanol in water, B=95% methanol in water). The HPLC traces were compared and the fractions comprising the extra peak obtained from the F017 and F018 mixture were collected and used as F017-F018 peptide complex.

In a similar manner, the peptides Val-Met-Ala-Glu-Val-Asp-Gly-Thr-Cys-Tyr (SEQ ID NO: 1) and His-Cys-Lys-Lys (SEQ ID NO: 3) can be prepared.

Likewise, the peptide conjugate

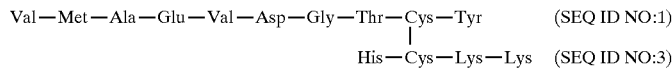

can also be prepared in the same manner.

EXAMPLE 2
Production of rabbit anti IgA-$\alpha_1$AT

New Zealand White rabbits were injected subcutaneously with 200 μg of purified human IgA-$\alpha_1$AT complex or 200 μg of peptide conjugate (F017-F018) emulsified in complete Freund's adjuvant, followed by further injections of the same amount of complex or peptide conjugate emulsified with incomplete Freund's adjuvant at 14 to 28 days. About a month later the animals were bled.

EXAMPLE 3
Isolation of IgG from rabbit antiserum and the preparation of various cleavaae fragments One volume of saturated $(NH_4)_2SO_4$ solution pH 6.5 was added to one volume of rabbit serum (to give a final salt concentration of 50% saturated), drop wise with stirring at 4° C.

After being left to stand for 6 hours, the precipitate was separated by centrifugation (3000 g for 30 minutes) and the supernatant was discarded. The precipitate was redissolved in 0.3 volumes of 0.01M phosphate buffer pH 8.0 and dialysed against 3 changes of the same buffer. This final dialysed solution (e.g. 5 ml) was placed on a DEAE-Sephadex column (e.g. 12.0×1 cm) which was pre-equilibrated with 0.01M phosphate buffer pH 8.0, and eluted with the same buffer. 2.0 ml fractions were collected. The fractions corresponding to the protein (i.e. IgG) peak were pooled and concentrated by ultrafiltration. Further IgG containing fractions were retrieved from the column by application of a salt gradient (i.e. 0.01M–0.10M $PO_4$), using 3 column volumes of each buffer in a gradient maker.

The composition of all fractions was recovered and checked by immunoelectrophoresis against anti-whole human serum; and those fractions containing only IgG were pooled, concentrated by ultrafiltration and stored below −20° C.

Preparation of proteolytic cleavage fragments (a) Preparation of Fab' and Fc fragments Native IgG is hydrolysed in the hinge region by papain to yield two antigen-binding fragments, Fab' and one dimer of the C-terminal half of the heavy chain, Fc' (Porter 1959). These are all of similar size (50,000 molecular weight) but they can be separated by ion-exchange chromatography. In general, proteolytic fragments of immunoglobulins can be separated under non-denaturing conditions because they are not held by non-covalent bonds.

Procedure:

1. Dissolve 1 mg of papain in 100 µl of 0.1M sodium phosphate buffer and quickly add 50 µl of this to the IgG. Mix gently and incubate at 37° C. overnight (16 hours).
2. Dialyze against water and then 3×500 ml of 0.01M sodium acetate pH 5.5
3. Equilibrate the ion exchanger with the 0.01M acetate buffer and pack into the column, wash with the same buffer at room temperature.
4. When both sample and exchanger are fully equilibrated, apply the sample to the column and elute with at least 60 ml of starting buffer until the absorbance at 280 nm has returned to baseline. Then apply a linear gradient, total volume 200 ml, from 0.01M to 1M acetate all at room temperature. Collect 5 ml fractions and monitor the absorbance at 280 nm.
5. Protein eluted with the starting buffer and the first peak in the gradient consists mostly of Fab'. The third peak is Fc. The protein yield in the three peaks should be about 90% of the original IgG.

(b) Preparation of F(ab')$_2$, Fab' and pFc' fragments

Native IgG is also hydrolysed by pepsin. However, this enzyme cleaves on the C-terminal side of at least one α-α-chain disulphide bond to give a divalent antigen-binding fragment, F(ab')2. It also degrades part of the Fc portion to small peptides to leave a dimer of the C-terminal quarter of the α-chain, pFc'. The F(ab')$_2$ fragment can be reduced to the monovalent Fab' fragment.

Procedure:

1. Dissolve 2 mg of protein in 200 µl of the acetate buffer and add 100 µl of this to the IgG solution. Mix gently and incubate at 37° C. overnight (16 hours).
2. Neutralize with 2M tris (approximately 300 µl—this irreversibly inactivates the enzyme) and centrifuge at 2000 g for 10 minutes to remove any precipitate.
3. Apply the supernatant to the G-200 column and elute with TBS. Collect 2.5 ml fractions and monitor the absorbance at 280 nm.
4. The first major peak is F(ab')$_2$. In front of this is undigested material and just behind it any Fab' or intact Fc formed. These minor products are sometimes not completely resolved from F(ab')$_2$ and form shoulders on the main peak. pFc' in the next peak and small peptides are eluted in the total column volume Fab'. F(ab')$_2$ can be directly reduced to Fab', if required, by the following procedure:

A. Pool the fractions containing F(ab')$_2$ and concentrate to 5 ml (this should give a protein concentration of about 6 mg/ml). Add 0.5 ml of the 1M tris buffer and 50 µl of EDTA solution.
B. Add 50 µl of dithiothreitol solution (0.1M dithiothreitol in 1M tris buffer, freshly prepared) and incubate in a sealed tube at room temperature for 1 hour with stirring.
C. Cool on ice, cover with foil and add 50 µl of iodoacetamide solution. Incubate in an ice bath for 30 minutes with stirring.
D. Add 5 µl of dithiothreitol solution, incubate at room temperature for 15 minutes and apply the mixture to the G-200 column. Elute as for the peptic digest. There will be a small peak of undissociated F(ab')$_2$ in its original position followed by a major peak of Fab'.

EXAMPLE 4

Assessment of specificity of rabbit (polyclonal) anti-complex antisera 96-well flexible assay plates (Falcon 3912) were coated with antigen, by overnight incubation at 4° C. with 120 µl aliquots of one of the following:

(i) IgA-α$_1$AT (5 µg/ml)
(ii) IgA (5 µg/ml)
(iii) α$_1$AT (5 µg/ml)

made up in 0.05M carbonate/bicarbonate buffer (pH 9.6).

The plates were then washed 3 times for 1 minute each with phosphate buffered saline (PBS), pH 7.2 containing 0.51% Tween 20 (PBS/Tween).

Normal (NRS) and test (anti-complex) rabbit sera (100 µl), as prepared in Example 2, were titrated in PBS/Tween (neat to 1 in 2 dilutions or neat to 1 in 5 dilutions) and added to the antigen coated plates. The plates were then incubated for 1 hour at –37° C. (Negative Control: PBS/Tween used alone or blank plate, incubated with normal rabbit serum). The plates were washed after incubation as before.

100 µl aliquots of goat-anti-rabbit/IgG/horseradish-peroxidase were added at a dilution of 1/1000 PBS/Tween and the plates were then incubated for 1 hour at 37° C. After incubation, the plates were washed as before.

100 µl aliquots of substrate were added, the substrate comprising:

20 mg o-phenylenediamine;
250 µl H$_2$O$_2$; and
50 ml 0.15M citrate phosphate buffer (pH 5).

The colour was allowed to develop for 5–15 minutes and then the enzymatic colour reaction was stopped by addition of 25 µl of 25% H$_2$SO$_4$ to all wells.

The optical density of the contents of each well was read at 492 nm (OD492) in a Titertek automated plate reader. The results set forth in Table 1 indicate that the antisera had a considerable specificity for the complex, giving a high OD492 at high antibody dilutions, some reaction towards α$_1$AT and no significant difference over controls towards IgA.

TABLE 1

Assessment of specificity of polyclonal rabbit anti-IgA-α$_1$AT complex antiserum by ELISA.
Mean zeroed values of optical density measured at 492 nm.

ANTIGEN COATING ON ELISA PLATE

| | IgA (5 µg/ml) | | α$_1$AT (5 µg/ml) | | IgA-α$_1$AT (5 µg/ml) | |
|---|---|---|---|---|---|---|
| Antibody dilution | NRS | anti-complex antibody | NRS | anti-complex antibody | NRS | anti-complex antibody |
| Neat | 0.761 | 0.644 | 0.652 | 1.519 | 0.364 | 1.388 |
| ½ | 0.665 | 0.703 | 0.585 | 1.526 | 0.754 | 1.447 |
| ¼ | 0.452 | 0.496 | 0.353 | 1.536 | 0.551 | 1.455 |
| ⅛ | 0.254 | 0.250 | 0.235 | 1.558 | 0.362 | 1.457 |
| 1/16 | 0.117 | 0.172 | 0.176 | 1.573 | 0.253 | 1.456 |
| 1/32 | 0.046 | 0.083 | 0.094 | 1.514 | 0.143 | 1.452 |
| 1/64 | — | 0.035 | — | 1.425 | 0.082 | 1.445 |
| 1/128 | — | 0.005 | — | 1.425 | 0.052 | 1.436 |
| 1/256 | — | — | — | 1.04 | 0.016 | 1.435 |
| 1/512 | — | — | — | 0.799 | 0.001 | 1.412 |
| 1/1024 | — | — | — | 0.489 | — | 1.284 |
| 1/2048 | — | — | — | 0.276 | — | 1.191 |

EXAMPLE 5
Production of monoclonal antibodies

Immunisation

BALB/c mice were injected intraperitoneally (i.p.) with 50 μg IgA-$\alpha_1$AT complex emulsified in equal volumes of Freund's complete adjuvant. Injections were repeated on day 14 and 28 with IgA-$\alpha_1$AT complex emulsified in Freund's incomplete adjuvant. Test tail bleeds taken on day 28 or later were assayed for the presence of anti-peptide antibodies by indirect ELISA. Three days prior to fusion, mice showing raised serum antibody titres received a further booster injection (i.p.) of 50 μg IgA-$\alpha_1$AT complex in PBS.

Fusion

Hyperimmunized mice were sacrificed by cervical-dislocation, the spleen removed and cells isolated and washed. The spleen cells were fused with a mouse myeloma cell line (Ag. 8.653 or NS0 or NS1) from a culture in logarithmic growth. By modification of the Köhler and Milstein method (Köhler, G. and Milstein, C., Nature (London) 256, pp. 495 (1975)), spleen and myeloma cells were fused at a ratio of 2:1, respectively, using 40% PEG (polyethylene glycol—mol. weight 1450). 1 ml PEG was added dropwise over a 1 minute time period to the pellet of mixed cells (spleen and myeloma) and diluted with serum-free medium. The fusion suspension was distributed into 96-well plates and cultured in medium containing HAT (Hypoxanthine, aminopterin and thymidine). The poor growth of hybridoma cells was rectified by the addition of normal mouse spleen cells (immediately after fusion), as a source of fresh macrophages to replace those cytolysed by the injected IgA-$\alpha_1$AT complex.

After 10 days, plates were examined for growth of hybridomas. Supernatant removed from these cells was screened for the presence of anti-IgA-$\alpha_1$AT complex antibodies by indirect ELISA. The following binding scheme was employed (*=labelled substance):

Support/IgA-$\alpha_1$AT/Anti-IgA-$\alpha_1$AT/goat anti-mouse IgG*

Cloning

When positive wells were identified as producing the desired antibody, the hybrid cells were cloned by limiting dilution and clones assayed again. Hybridomas were cultured in flasks or grown in mice. Ascitic fluid was raised in BALB/c mice primed with pristane (0.5 ml injected i.p.) a few days prior to injecting with $10^5$ hybrid cells. Tumour formation should result after some 2–4 weeks and accumulated ascitic fluid removed by sacrificing the mouse and removing the contents of the abdominal cavity with a pipette. The concentration of monoclonal antibody in ascitic fluid was determined at every tumour passage; this ranged from 5–15 mg/ml.

Screening

The procedure employed in screening the monoclonal antibodies was as follows. Plates were prepared comprising the following layouts:

(a) plate coated with human IgA-$\alpha_1$AT complex (by incubation with a solution containing 5 μg protein/ml) +cell supernatant+goat anti-mouse-peroxidase labelled antibody;

(b) plate coated with free human IgA (5 μg/ml solution) +subsequent steps as above;

(c) plate coated with free human $\alpha_1$AT (5 μg/ml solution) +subsequent steps as above.

Cells producing those supernatants which reacted positively only in system (a) above, were selected as hybridomas which were producing monoclonal antibody directed specifically against the IgA-$\alpha_1$AT complex (whilst being unreactive with free IgA or free $\alpha_1$AT).

Two such hybridoma cell lines, secreting monoclonal antibodies to the naturally occurring IgA-$\alpha_1$AT complex, have been deposited at the European Collection of Animal Cell Cultures, PHLS Centre for Applied Microbiology and Research, Porton Down. Salisbury, Wiltshire SP4 OJG, England. The first, designated NLW.54, was deposited on 6th Feb. 1990 under the accession number ECACC 90020611, under the provisions of the Budapest Treaty on the International Recognition of the Deposit of Microorganisms for the Purposes of Patent Procedure. The most preferred antibody, designated NLW.50, was deposited on 13th Dec. 1990 under the accession number ECACC 90121302, also under the provisions of the Budapest Treaty.

EXAMPLE 6
Measurement of IgA-$\alpha_1$AT complex by 2-Dimensional Immunoelectrophoresis (2D-IEP)

A solution of 1% agarose (Sea kem HGT Agarose ICN Biomedical Ltd.) in 0.05M barbitone buffer pH 8.6 was prepared. 4 ml of this melted agarose solution was poured onto a 7.6×5.0 cm glass plate and allowed to set, whereupon 1.1×5.0 cm strips were cut and transferred onto clean 7.6×5.0 cm glass plates (1 strip of agarose per plate). A 2 mm diameter well was cut into the agarose, 15 mm from the left edge and 7 mm from the bottom of the plate. 3 μl of the test serum was applied to the well and a small spot of bromophenol blue was added to the sample. The plates were placed onto the electrophoresis apparatus with the sample well nearest the cathode and the agarose strip running lengthways to the anode. Filter paper wicks were placed on the agarose, 1 cm in from each end. The plates were then electrophoresed at 20 mA/6 plates with cooling, until the slower moving (albumin bound) bromophenol blue marker spot reached the wick on the anode side of the apparatus (approximately 2 hours). 50 μl of sheep anti-human $\alpha_1$AT was added to 4 ml of melted agarose at 56° C. and poured onto the glass plates into the space above the 1.1×7.6 cm strip. The plates were then electrophoresed at 90° to the first electrophoresis at 20 mA/6 plates overnight. The plates were removed from the electrophoresis apparatus and placed between weighted filter paper for 30 minutes. The plates were then transferred to an incubator until fully dried. The plates were stained with 0.05% Coomassie Brilliant Blue (Coomassie is a Registered Trade Mark) for 10 minutes and then destained with methanol/acetic acid/water (40:4:56) until precipitin lines could clearly be seen. The area of the 'slower' moving peak (IgA-$\alpha_1$AT complex) was measured using a planimeter, and the complex concentration quoted as area in cm².

The concentration of IgA-$\alpha_1$AT complex in a panel of test pathological specimens was measured by this method. The results are set forth in Table 2 below.

TABLE 2

| Patient | Diagnosis | Specimen | IgA-#1AT Complex Concentration (2D-IEP value) (Arbitrary units) | 2D-IEP Rank |
|---|---|---|---|---|
| 1 | RA | Serum | 4.05 | 4 |
| 2 | RA | Serum | 2.80 | 5 |
| 3 | Swollen Knee | Serum | 1.00 | 9 |
| 4 | RA | Serum | 2.40 | 7 |
| 5 | AS | Serum | 0.45 | 10 |
| 6 | IgA myelomatosis | Serum | 26.00 | 1 |
| 7 | IgA myelomatosis | Serum | 12.00 | 2 |
| 8 | RA | Joint Fluid | 2.80 | 5 |
| 9 | RA | Serum | 6.85 | 3 |

TABLE 2-continued

| Patient | Diagnosis | Specimen | IgA-#1AT Complex Concentration (2D-IEP value) (Arbitrary units) | 2D-IEP Rank |
|---|---|---|---|---|
| 10 | Polymyalgia | Serum | 0.70 | 11 |
| 11 | RA | Serum | 1.20 | 8 |
| 12 | RA* | Joint Fluid | 0.00 | 12 |

RA = Rheumatoid Arthritis
AS = Ankylosing Spondylitis
* = Steroid treated patient

EXAMPLE 7

Measurement of IgA-$\alpha_1$AT complex by sandwich ELISA assays General method

A 96-well flexible assay plate (Falcon 3912) was coated with a first or capture antibody of optimal concentration made up in a coating buffer (0.05M carbonate/bicarbonate buffer pH 9.6). 120 μl aliquots of this antibody (e.g. 1/16000 dilution) were adsorbed onto the plate by incubation at 37° C. for 1 hour, room temperature for 1 hour or overnight at 4° C. The plate was then washed 3 times for 1 minute each time with phosphate buffered saline (pH 7.2) containing 0.05% Tween 20.

100 μl aliquots of IgA-$\alpha_1$AT complex or test serum samples (diluted 2 fold or 5 fold) were added to the plate and incubated for 1 hour at 37° C. The plates were then washed as before.

100 μl aliquots of a second antibody of optimal concentration (e.g. 1/6000 Rabbit-anti-IgA-$\alpha_1$AT complex) were added to the plate and then incubated at 37° C. for 1 hour. The plate was again washed as before. Then, 100 μl aliquots of a third antibody of optimal dilution were added. This antibody (e.g. Goat-anti-Rabbit IgG) was labelled with the enzyme horseradish peroxidase. The plates were incubated at 37° C. for 1 hour and then washed as before.

100 μl aliquots of the substrate for the enzyme horseradish peroxidase was added. The substrate comprised 20 mg o-phenylenediamine, 250 μl $H_2O_2$ and 50 ml 0.15M citrate-phosphate buffer, pH 5.0. The colour was allowed to develop for 5–15 minutes and then the enzymatic colour reaction was stopped by the addition of 25 μl of 25% $H_2SO_4$ to all the wells. The optical density of the contents of each well was read at 492 nm (OD492) in a Titertek automated plate reader.

Results:

1. Sandwich ELISAs incorporating polyclonal antibodies directed against IgA or $\alpha_1$AT. The capture antibody is anti-IgA The procedure for carrying out the sandwich ELISA was as described above. 4 assays were carried out employing 2 sheep and 2 rabbit polyclonal anti-IgA antibodies as the capture or first antibody. The binding schemes for these ELISA assays are shown below:

Assay 1: Support/Sh.(1)anti-IgA/IgA-$\alpha_1$AT complex/ Sh.anti-$\alpha_1$AT+labelled anti-sheep antibody.

Assay 2: Support/Sh.(2)anti-IgA/IgA-$\alpha_1$AT complex/ Sh.anti-$\alpha_1$AT+labelled anti-sheep antibody.

Assay 3: Support/Rb.(1)anti-IgA/IgA-$\alpha_1$AT complex/ Sh.anti-$\alpha_1$AT+labelled anti-sheep antibody.

Assay 4: Support/Rb.(2)anti-IgA/IgA-$\alpha_1$AT complex/ Sh.anti-$\alpha_1$AT+labelled anti-sheep antibody.

Sh.=Sheep
Rb.=Rabbit

The results of the above assays 1–4 are set forth in Table 3 below. The samples 1–12 are the same as those samples in Table 2 of Example 6, where the concentrations of IgA-$\alpha_1$AT complex were measured by 2D-IEP. Their rankings in the 2D-IEP are reproduced in Table 3 for ease of comparison.

TABLE 3

| Sample No. | Assay 1 OD492 | Rank | Assay 2 OD492 | Rank | Assay 3 OD492 | Rank | Assay 4 OD492 | Rank | Rank in 2D-IEP |
|---|---|---|---|---|---|---|---|---|---|
| 1. | 0.828 | 2 | 0.355 | 2 | 0.900 | 2 | 0.355 | 2 | 4 |
| 2. | 0.924 | 1 | 0.578 | 1 | 1.157 | 1 | 0.578 | 1 | 6 |
| 3. | 0.657 | 7 | 0.173 | 4 | 0.176 | 5 | 0.173 | 4 | 9 |
| 4. | 0.607 | 9 | 0.153 | 9 | 0.144 | 11 | 0.153 | 9 | 7 |
| 5. | 0.580 | 10 | 0.164 | 7 | 0.141 | 12 | 0.164 | 7 | 10 |
| 6. | 0.702 | 4 | 0.160 | 8 | 0.155 | 8 | 0.160 | 8 | 1 |
| 7. | 0.664 | 6 | 0.167 | 6 | 0.147 | 10 | 0.167 | 6 | 2 |
| 8. | 0.653 | 8 | 0.158 | 10 | 0.191 | 4 | 0.148 | 10 | 5 |
| 9. | 0.406 | 12 | 0.116 | 12 | 0.157 | 7 | 0.116 | 12 | 3 |
| 10. | 0.762 | 3 | 0.170 | 5 | 0.566 | 3 | 0.170 | 5 | 11 |
| 11. | 0.663 | 5 | 0.178 | 3 | 0.154 | 9 | 0.178 | 3 | 8 |
| 12. | 0.466 | 11 | 0.132 | 11 | 0.159 | 6 | 0.132 | 11 | 12 |

As can be seen qualitatively by comparing the rankings and can be confirmed by statistical analysis, the ELISA failed to confirm the results of the 2D-IEP. For example, in assays 1 and 3, samples 6, 7 and 9 all gave low values despite their high 2D-IEP values, the concentration of complex in sample 10 appeared low by 2D-IEP but high by ELISA value.

In assays 2 and 4, samples 6, 7 and 9 all gave low ELISA values, despite their high 2D-IEP values. These results show that this approach cannot be used to measure IgA-$\alpha_1$AT complex. The discrepancies in results obtained by the two methods (ELISA and 2D-IEP) are probably due to the free IgA binding preferentially to the anti-IgA antibody coating the ELISA plate, thereby preventing the binding of IgA-$\alpha_1$AT complex.

2. Sandwich ELISA systems incorporating polyclonal antibodies directed against IgA or $\alpha_1$AT. The capture antibody is anti-$\alpha_1$AT A sandwich ELISA procedure was carried out as described above. The following binding scheme was used:

Support/Sh.anti-$\alpha_1$AT/IgA-$\alpha_1$AT complex/polyclonal anti IgA+labelled antibody In this Example, different pathological specimens were measured and compared to measurements of the same samples by 2D-IEP. The results are shown in Table 4 below:

TABLE 4

| Patient's Name | Diagnosis | ELISA results+ at serum diln. of: | | | | Complex level determ. by 2 Dimen. I.E.* |
|---|---|---|---|---|---|---|
| | | 1/5 | 1/10 | 1/20 | 1/40 | |
| Weaver | RA | 0.98 | 0.94 | 0.85 | 0.77 | 4.05 |
| Whyte | " | 1.03 | 0.91 | 0.72 | 0.52 | 2.80 |
| Reid | " | 0.71 | 0.45 | 0.21 | 0.08 | 1.00 |
| Barton | " | 0.11 | 0.10 | 0.08 | 0.07 | 2.40 |
| Wright | " | 0.22 | 0.12 | 0.09 | 0.06 | 0.45 |
| Snape | " | 0.12 | 0.10 | 0.09 | 0.06 | 1.00 |
| Albandol | Myeloma | 0.07 | 0.09 | 0.08 | 0.06 | 26.00 |
| Jones | " | 0.13 | 0.12 | 0.09 | 0.07 | 12.00 |

+ = OD (optical density) units
* = arbitrary units

The wide differences in the results obtained by the two methods, as seen e.g. in the rankings, are probably attributable to the binding of free $\alpha_1AT$ to the coating antibody preferentially, thereby inhibiting binding of the IgA-$\alpha_1$AT complex.

3. ELISA sandwich assays employing antibody (monoclonal or polyclonal) to the naturally produced complex as capture or first antibodies Carrying out a sandwich ELISA procedure as described, the following binding schemes were used:

1. Support/Mc.anti-IgA-$\alpha_1$AT/Iga-$\alpha_1$AT complex/Sh.Pc.anti-IgA +labelled anti-sheep antibody.
2. Support/Mc.anti-IgA-$\alpha_1$AT/Iga-$\alpha_1$AT complex/Sh.Pc.anti-$\alpha_1$AT +labelled anti-sheep antibody.
3. Support/Mc.anti-IgA-$\alpha_1$AT/IgA-$\alpha_1$AT complex/Rb. anti IgA-$\alpha_1$AT+labelled anti-rabbit antibody.
4. Support/Rb.Pc.anti-IgA-$\alpha_1$AT/IgA-$\alpha_1$AT complex/Sh.Pc. anti-IgA+labelled anti-sheep antibody.
5. Support/Rb.Pc.anti-IgA-$\alpha_1$AT/IgA-$\alpha_1$AT complex/Sh.Pc. anti-$\alpha_1$AT+labelled anti-sheep antibody.
6. Support/Rb.Pc.anti-IgA-$\alpha_1$AT/IgA-$\alpha_1$AT complex/Mc. anti-IgA-$\alpha_1$AT+labelled antibody.

Pc.=Polyclonal antibody raised against the purified complex, IgA or $\alpha_1$AT as indicated in the above binding schemes.

Mc.=Monoclonal antibody secreted by hybridoma NLW54 in accordance with the invention.

Sh.=Sheep.

Rb.=Rabbit.

The results of a sandwich ELISA incorporating binding scheme (3) above are shown in Table 5 below. This table shows a comparison of OD492 values obtained from the ELISA with results from 2D-IEP.

TABLE 5

| Serum No. | 2D-IEP | | ELISA (OD492) | |
|---|---|---|---|---|
| | Values | Rank | Values | Rank |
| 19 | 0.9 | 10 | 0.65 | 5 |
| 20 | 0.5 | 11 | 0.64 | 9 |
| 21 | 1.5 | 9 | 0.63 | 6 |
| 22 | 2.3 | 8 | 0.63 | 6 |
| 23 | 2.5 | 7 | 0.63 | 6 |
| 24 | 2.9 | 6 | 0.60 | 10 |
| 25 | 3.2 | 5 | 0.77 | 3 |
| 26 | 3.5 | 4 | 0.60 | 10 |
| 27 | 3.9 | 3 | 0.76 | 4 |
| 28 | 5.0 | 2 | 0.81 | 2 |

TABLE 5-continued

| Serum No. | 2D-IEP | | ELISA (OD492) | |
|---|---|---|---|---|
| | Values | Rank | Values | Rank |
| purified IgA-$\alpha_1$AT (2 mg/ml) | isolated complex (7.0) | 1 | 0.99 | 1 |

As seen in Table 5 above, three of the four samples from binding scheme (3) giving high 2D-IEP values (>3.0 units) also show higher OD492 values. Although in serum samples containing lower levels. of IgA-$\alpha_1$AT complex, there is little difference in the ELISA values measured, this result may be remediable by increasing the sensitivity of the assay.

The results from ELISA assays incorporating binding schemes 1 and 2 (data not shown) reveal a similar trend to that for scheme (3). These results show that in a sandwich assay the detection antibody can be anti- to the whole complex or to either component thereof.

The results obtained from assays incorporating binding schemes 4, 5 and 6 reveal that it is not possible to measure the IgA-$\alpha_1$AT complex by using plates coated with polyclonal rabbit anti-complex antibody (data not shown).

EXAMPLE 8

Measurement of IgA-$\alpha_1$AT complex by inhibition ELISA

A 96-well rigid plate (Falcon 3040) was coated with 500 $\mu$g ml$^{-1}$ bovine serum albumin (BSA). Aliquots of 200 $\mu$l were added to each well and the plate was incubated at 37° C. for 1 hour. The plate was washed three times for 1 minute each time with phosphate buffered saline (PBS) pH 7.2 containing 0.05% Tween 20 (PBS/Tween 20). 100 $\mu$l aliquots of IgA-$\alpha_1$AT complex or test serum samples were titrated (2 fold or 5 fold dilutions in PBS/Tween 20) then 100 $\mu$l aliquots of monoclonal antibody to the IgA-$\alpha_1$AT complex from the NLW54 cell line were added to an optimal concentration (e.g. 1/20000 to give a final concentration of 1/40000) and the plate was incubated overnight at 4° C.

After the overnight incubation described above, the plate was centrifuged at 3000 rpm for 15 minutes, and 90 $\mu$l aliquots were transferred from each well onto another plate pre-coated with IgA-$\alpha_1$AT complex. This plate was pre-coated as follows. A 96-well flexible assay plate (Falcon 3912) was coated with 100 $\mu$l aliquots of IgA-$\alpha_1$AT complex of 5 $\mu$g ml-1 concentration, made up in coating buffer (0.05M carbonate/bicarbonate buffer pH 9.6). This plate was then incubated at 37° C. for 1 hour, room temperature for 2 hours or 4° C. overnight and then washed as described above.

100 $\mu$l aliquots of antibody labelled with the enzyme horseradish peroxidase, of optimal dilution (e.g. labelled goat anti-mouse IgG at 1/1000 dilution) were added and the plate was incubated at 37° C. for 1 hour. The plate was washed as before. 100 $\mu$l aliquots of substrate solution were added. The substrate solution comprised 20 mg o-phenylenediamine, 250 $\mu$l H$_2$O$_2$ and 50 ml 0.15M citrate phosphate buffer, pH 5.0. The colour was allowed to develop for 5–15 minutes before the enzymatic reaction was terminated by adding 25 $\mu$l of 25% H$_2$SO$_4$ to all the wells.

The optical density of the contents of each well was read at 492 nm (OD492) in a Titertek automated plate reader. The calculation of percentage inhibition was as follows:

$$\% \text{ inhibition} = 1 - \frac{OD492 \text{ sample} - OD492 \text{ blank}}{OD492 \text{ uninhibited sample} - OD492 \text{ blank}} \times 100$$

The results of this assay are shown in Table 6. The results were compared to measurement of the same sera by a conventional 2D-IEP procedure. The ELISA results are expressed in terms of the reciprocal of the dilution of serum (the titre) required to be added to give 507. inhibition of the labelled antibody.

TABLE 6

| Rheumatoid Serum | Reciprocal of Serum titre giving 50% inhibition | Rank | 2D-IEP (Arbitrary Area Units) | 2D-IEP Rank |
|---|---|---|---|---|
| 29 | 423 | 3 | 0.75 | 3 |
| 30 | 1405 | 5 | 1.15 | 4 |
| 31 | 1553 | 7 | 1.90 | 5 |
| 32 | 2051 | 8 | 2.45 | 6 |
| 33 | 1494 | 6 | 2.50 | 7 |
| 34 | 1310 | 4 | 2.75 | 8 |
| 35 | 52 | 1 | 0.60 | 1 |
| 36 | 344 | 2 | 0.65 | 2 |

As will be seen from the rankings in Table 6, there was a good agreement between the ELISA and the 2D-IEP. This has been calculated statistically as about 69%. This percentage is even more impressive (89%) if the results for serum 32 (the sample giving the highest ELISA inhibition value) are ignored.

EXAMPLE 9

Measurement of IgA-$\alpha_1$AT complex by a double antibody capture ELISA 96-well flexible assay plates (Falcon 3912) were coated with capture antibody of optimal concentration made up in coating buffer (0.05M carbonate/bicarbonate; pH 9.6).

Aliquots (120 $\mu$l) of antibody at 1/1000 dilution were absorbed onto a plate by incubation at 37° C. for 1 hour, at room temperature for 2 hours or at 4° C. overnight. The plate was then washed (3×1 minute) with phosphate-buffered saline (PBS), pH 7.2, containing 0.05% Tween 20.

To the above pre-coated plate, monoclonal antibody to IgA-$\alpha_1$AT complex as secreted by hybridoma NLW54 in accordance with the invention, was added and the assay carried out according to the protocol previously described in Example 7. The following binding scheme was employed:

Support/Mc. rat anti-mouse IgG/Mc mouse anti-IgA-$\alpha_1$AT complex/IgA-$\alpha_1$AT complex/Pc.Rb. anti-IgA-$\alpha_1$AT/labelled anti-rabbit antibody Mc.=Monoclonal antibody Pc.=Polyclonal antibody Rb.=Rabbit The results of determining the level of Ig-$\alpha_1$AT complex in a panel of test sera (rheumatoid arthritis and normal controls) by the above double antibody capture method were compared with the levels of IgA-$\alpha_1$AT complex measured by 2D-immunoelectrophoresis, single antibody capture ELISA (as described in Example 7(3) following binding scheme 3) and inhibition ELISA techniques (as described in Example 8). These results are shown in Table 7.

TABLE 7

| Sample | 2D-IEP (cm$^2$) | Double Ab ELISA (serum dil. 1/40 O.D. 492 nm | Single Ab ELISA (serum dil. 1/40 O.D. 492 nm | Inhibition ELISA 50% Inhibition Titre |
|---|---|---|---|---|
| 29 | 0.5 | 0.298 | 0.674 | 196 |
| 30* | 1.2 | 0.564 | 0.877 | 309 |
| 31 | 3.3 | 0.342 | 0.654 | 221 |
| 32 | 3.9 | 0.538 | 0.748 | 356 |
| Normal sera | 1.1 | 0.310 | 0.644 | 202 |
| Complex - containing sera | 5.2 | 0.571 | 0.79 | 443 |

This sample (*) is anomalous in that it consistently shows high ELISA values and low 2D-IEP values. It is probably giving false low 2D-IEP readings.

EXAMPLE 10

Comparison of results from employing murine monoclonal NLW.50 and NLW.54 in ELISA system A double antibody capture assay was also carried out in which the monoclonal antibody to IgA-$\alpha_1$AT complex was secreted by hybridoma NLW.50 in accordance with the invention. In this assay, polystyrene plates were employed (Dynatech-Immulon 4). The assay was carried out as described above in Example 9 except that the test serum was diluted 1/100. The use of a better monoclonal antibody coupled with the use of polystyrene plates contributed to the increased sensitivity of this assay. The following binding scheme was employed:

port/Rat Mc Anti-mouse IgG/Mc anti-IgA-$\alpha_1$AT/IgA-$\alpha_1$AT complex/Rb Pc anti-IgA-$\alpha_1$AT/labelled goat anti-rabbit antibody.

Mc=Monoclonal antibody

Pc=Polyclonal antibody

G=Goat

Rb=Rabbit

The results are shown in Table 8 below.

TABLE 8

| SERUM SAMPLE | 2D-IEP RESULTS (arbitrary units) | | ELISA RESULTS (OD 492) | | | |
|---|---|---|---|---|---|---|
| | | | NLW.50 | | NLW.54 | |
| | Value | Rank | Value | Rank | Value | Rank |
| 37 | 0.75 | 10 | 0.572 | 10 | 0.634 | 8 |
| 38 | 1.20 | 9 | 0.628 | 9 | 0.596 | 10 |
| 39 | 1.40 | 8 | 0.685 | 7 | 0.635 | 7 |
| 40 | 2.00 | 7 | 0.724 | 6 | 0.634 | 8 |
| 41 | 2.50 | 6 | 0.882 | 1 | 0.663 | 5 |
| 42 | 2.75 | 5 | 0.851 | 3 | 0.813 | 2 |
| 43 | 3.30 | 3 | 0.651 | 8 | 0.637 | 6 |
| 44 | 3.60 | 2 | 0.868 | 2 | 0.897 | 1 |
| 45 | 4.40 | 1 | 0.756 | 5 | 0.679 | 4 |
| 46 | 3.00 | 4 | 0.781 | 4 | 0.712 | 3 |
| 47 | 0.60 | 11 | 0.386 | 11 | 0.374 | 11 |

When the results are plotted as ELISA results for NLW.54 and NLW.50 vs the 2D-IEP measurement, then the correlation coefficient are 0.56 and 0.72 respectively—confirming that NLW.50 is slightly more sensitive than NLW.54 and the reason why it is thus the preferred antibody.

EXAMPLE 11

Effect of having one or two detection antibodies in a double antibody capture ELISA assay A double antibody capture ELISA assay was carried out as previously described in Example 9 except that polystyrene plates (Dynatech-Immulon 4) were employed and the test sera was diluted 1/100. The effect of using one or two detection antibodies in the ELISA assay was investigated. The following binding schemes were employed:

(1) support/Rat Mc anti-mouse IgG/Mouse Mc anti-IgA-$\alpha_1$AT/IgA-$\alpha_1$AT complex/Sh Pc anti-IgA/D anti Sheep labelled antibody.

(2) support/Rat Mc anti-mouse IgG/Mouse Mc anti-IgA-$\alpha_1$AT/IgA-$\alpha_1$AT complex/Sh Pc anti-IgA labelled.

Mc=Monoclonal antibody
Pc=Polyclonal antibody
Sh=Sheep
D=Donkey

The monoclonal anti-IgA-$\alpha_1$AT antibody was that secreted by hybridoma NLW.50 in accordance with the invention.

The results are shown in Table 9 below.

TABLE 9

| SERUM | IgA-$\alpha_1$AT COMPLEX CONCENTRATION (arbitrary units) | | SERUM | IgA-$\alpha_1$AT COMPLEX CONCENTRATION (arbitrary units) | |
|---|---|---|---|---|---|
| | Binding Scheme 1 | Binding Scheme 2 | | Binding Scheme 1 | Binding Scheme 2 |
| 2 | 3.0 | 5.0 | 30 | 0.32 | 0.38 |
| 3 | 0.3 | 0.39 | 31 | 0.58 | 1.05 |
| 4 | 0.43 | 0.9 | 32 | 0.27 | 0.47 |
| 5 | 0.8 | 1.9 | 33 | 0.36 | 0.84 |
| 6 | 0.4 | 0.52 | 34 | 0.33 | 0.39 |
| 10 | 0.5 | 0.8 | 36 | 0.54 | 1.05 |
| 12 | 0.55 | 1.1 | 37 | <0.2 | 0.29 |
| 14 | 0.36 | 0.66 | 38 | 0.3 | 0.40 |
| 15 | 0.52 | 0.67 | 40 | 0.45 | 0.57 |
| 16 | 0.41 | 0.8 | 41 | 0.34 | 0.61 |
| 17 | 0.72 | | 42 | 0.32 | 0.45 |
| 18 | 0.35 | 0.53 | 44 | 0.325 | 0.34 |
| 19 | 0.41 | 0.67 | 45 | 0.53 | 0.69 |
| 20 | 0.6 | 1.45 | 47 | 0.35 | 0.41 |
| 22 | 0.49 | 1.1 | 48 | 0.275 | 0.35 |
| 23 | 0.45 | 0.63 | 49 | 0.44 | 0.74 |
| 24 | <0.2 | <0.2 | 50 | <0.2 | 0.3 |
| 25 | 0.39 | 0.48 | 51 | 0.52 | 0.85 |
| 26 | 0.75 | 1.7 | 52 | 0.46 | 0.69 |

The results of this assay show that there was no loss of sensitivity when employing one detection antibody instead of two as is the tradition in ELISA assays. This has the advantage of reducing the time needed for carrying out the assay by one hour, and the cost of carrying out such an assay is reduced also.

When comparing the results of the two assays by plotting the results gained for binding scheme 1 against binding scheme 2, the correlation coefficient was 0.88 and the standard deviation <0.001 which is highly significant. The point representing serum sample number 2 has been eliminated from this statistical analysis (if included the correlation coefficient is 0.97).

EXAMPLE 12

Comparison of ELISA sandwich assay employing one detection antibody only with 2D-IEP measurements A double antibody capture ELISA assay was carried out in accordance with the method described in Example 9. Polystyrene plates (Dynatech-Immulon 4) were employed and the test sera was diluted 1/100. The monoclonal capture antibody was that secreted by hybridoma NLW.50 in accordance with the invention. The following binding scheme was employed:

support/Rat Mc anti-Mouse IgG/Mc anti-IgA-$\alpha_1$AT/IgA-$\alpha_1$AT complex/Sh Pc anti-IgA/labelled D anti-sheep IgA antibody.

Mc=Monoclonal antibody
Pc=Polyclonal antibody
D=Donkey
Sh=Sheep

Measurement of IgA-$\alpha_1$AT complex by 2D-IEP was carried out according to Example 6. The results are shown in Table 10 below.

TABLE 10

| SERUM | 2D-IEP (cm$^2$) | | ELISA (arbitrary units) | |
|---|---|---|---|---|
| | Value | Rank | Value | Rank |
| 38 | 1.5 | 9 | 0.77 | 8 |
| 6 | 1.3 | 11 | 0.87 | 7 |
| 8 | 3.0 | 3 | 2.3 | 3 |
| 54 | 3.2 | 2 | 1.28 | 4 |
| 43 | 1.3 | 11 | 0.54 | 12 |
| 29 | 1.1 | 13 | 0.56 | 11 |
| 32 | 2.3 | 4 | 2.35 | 2 |
| 45 | 1.4 | 10 | 0.96 | 5 |
| 65 | 1.8 | 7 | 0.94 | 6 |
| 24 | 1.7 | 8 | 0.58 | 9 |
| 7 | 0.6 | 15 | 0.47 | 13 |
| 44 | 3.3 | 1 | 2.5 | 1 |
| 58 | 2.3 | 4 | 0.57 | 10 |
| 50 | 2.2 | 6 | 0.4 | 15 |
| 1 | 0.9 | 14 | 0.44 | 14 |

When these samples were plotted on a graph comparing 2D-IEP and ELISA, the correlation coefficient was 0.73, which is significant.

We claim:

1. A ligand comprising an antibody domain specific for an antigenic determinant of a complex of human IgA and $\alpha_1$-antitrypsin, said antibody domain being substantially non reactive with free human IgA and free human $\alpha_1$-antitrypsin.

2. A ligand according to claim 1 wherein said domain is specific for a naturally occurring complex of IgA and $\alpha_1$-antitrypsin (IgA-$\alpha_1$AT).

3. A ligand according to claim 1 wherein said domain is specific for a synthetic peptide comprising a first peptide fragment having an amino acid sequence found in the Fc region of human IgA and a second peptide fragment covalently bonded to the first, and having an amino acid sequence found in human $\alpha$1-antitrypsin, wherein the first and second fragments comprise SEQ ID NO: 2 and SEQ ID NO: 4.

4. A ligand according to claim 1, which is a monoclonal antibody to a naturally occurring complex of human IgA and $\alpha$1-antitrypsin.

5. A ligand according to claim 1, which is an Fab' fragment of said antibody.

6. A ligand according to claim 1, which is an F(ab')$_2$ fragment of said antibody.

7. An antibody produced by the hybridoma cell line designated NLW.50 deposited on 13th Dec. 1990 at the European Collection of Animal Cell Cultures PHLS Centre for Applied Microbiology and Research, Porton Down, Salisbury, Wiltshire SP4 OJG, England under the accession number ECACC 90121302.

8. A method of assay for detecting human rheumatoid arthritis (RA) in a patient which comprises:

contacting a body fluid sample suspected to contain a complex of human IgA and α1-antitrypsin (IgA-α1AT) with the ligand as claimed in claim 1, detecting immunological binding between said complex and and said ligand, and determining the existence of RA in said patient based on elevated levels of said immunological binding.

9. A method according to claim 8 wherein the assay is of a sandwich type and comprises capturing said IgA-$\alpha_1$AT by causing it to bind to said ligand, as a first capture ligand, and assaying said binding by causing said IgA-$\alpha_1$AT to bind to a second, labelled detection ligand which comprises an antibody domain capable of detecting said IgA-$\alpha_1$AT, and detecting or measuring the amount of label thus captured.

10. A method according to claim 9 wherein the assay is carried out in solution, the capture ligand is bound to an insoluble support, after said binding the support is separated from solution and the presence or amount of label on the support is detected or measured.

11. A method according to claim 8 or 9 wherein the detection ligand is an antibody to IgA, $\alpha_1$AT or a complex thereof.

12. An assay kit for carrying out a method of assay of human rheumatoid arthritis in a patient, the kit comprising:

(1) a ligand according to claim 1, and (2) an IgA-α1AT complex.

13. An assay kit according to claim 12 for use in a sandwich assay wherein said ligand is intended for use as a capture ligand, the complex is provided for testing the kit and which further comprises:

(3) a second ligand intended for use as a labeled or detection ligand, which comprises an antibody domain capable of detecting an IgA-α1AT complex.

14. An assay kit according to claim 12 for use in a competitive or inhibition assay in which the said IgA-$\alpha_1$AT complex component of the kit is a peptide F017-F018 comprising SEQ ID NO:2 and SEQ ID NO:4.

15. An assay kit according to claim 12, wherein the ligand is an antibody produced by the hybridoma cell line NLW.50 deposited on 13 Dec. 1990 at the European Collection of Animal Cell Cultures PHLS Centre for Applied Microbiology and Research, Porton Down, Salisbury, Wiltshire SP4 OJG, England under the accession number ECACC 90121302.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 10 amino acids
( B ) TYPE: amino acid
( C ) STRANDEDNESS: single
( D ) TOPOLOGY: linear (i i) MOLECULE TYPE: peptide (v) FRAGMENT TYPE: C-terminal (x i) SEQUENCE DESCRIPTION: SEQ ID NO: 1:

```
Val  Met  Ala  Glu  Val  Asp  Gly  Thr  Cys  Thr
1                  5                        10
```

(2) INFORMATION FOR SEQ ID NO: 2:

(i) SEQUENCE CHARACTERISTICS:
      (A) LENGTH: 13 amino acids
      (B) TYPE: amino acid
      (C) STRANDEDNESS: single
      (D) TOPOLOGY: linear (i i) MOLECULE TYPE: peptide (v) FRAGMENT TYPE: C-terminal (x i) SEQUENCE DESCRIPTION: SEQ ID NO: 2:

```
Val  Ser  Val  Val  Met  Ala  Glu  Val  Glu  Gly  Thr  Cys  Tyr
1                  5                        10
```

(2) INFORMATION FOR SEQ ID NO: 3:

(i) SEQUENCE CHARACTERISTICS:
      (A) LENGTH: 4 amino acids
      (B) TYPE: amino acid
      (C) STRANDEDNESS: single
      (D) TOPOLOGY: linear (i i) MOLECULE TYPE: peptide (v) FRAGMENT TYPE: internal (x i) SEQUENCE DESCRIPTION: SEQ ID NO: 3:

```
His  Cys  Lys  Lys
1
```

(2) INFORMATION FOR SEQ ID NO: 4:

(i) SEQUENCE CHARACTERISTICS:
      (A) LENGTH: 13 amino acids
      (B) TYPE: amino acid
      (C) STRANDEDNESS: single
      (D) TOPOLOGY: linear (i i) MOLECULE TYPE: peptide (v) FRAGMENT TYPE: internal (x i) SEQUENCE DESCRIPTION: SEQ ID NO: 4:

```
Gly  Met  Phe  Asn  Ile  Gln  His  Cys  Lys  Lys  Leu  Ser  Ser
1                  5                        10
```